(12) United States Patent
Maritan

(10) Patent No.: US 8,366,668 B2
(45) Date of Patent: Feb. 5, 2013

(54) AUTOINJECTOR WITH AUDIBLE INDICATION OF COMPLETED DELIVERY

(75) Inventor: Lionel Maritan, Pierre Chatel (FR)

(73) Assignee: Becton Dickinson France (FR)

( * ) Notice: Subject to any disclaimer, the term of this patent is extended or adjusted under 35 U.S.C. 154(b) by 0 days.

(21) Appl. No.: 13/120,769

(22) PCT Filed: Sep. 29, 2008

(86) PCT No.: PCT/IB2008/003257
§ 371 (c)(1),
(2), (4) Date: May 19, 2011

(87) PCT Pub. No.: WO2010/035057
PCT Pub. Date: Apr. 1, 2010

(65) Prior Publication Data
US 2011/0238014 A1 Sep. 29, 2011

(51) Int. Cl.
*A61M 5/20* (2006.01)
(52) U.S. Cl. .................................. 604/135
(58) Field of Classification Search ............ 604/110, 604/131, 134, 135
See application file for complete search history.

(56) References Cited

U.S. PATENT DOCUMENTS

| 5,599,309 | A | 2/1997 | Marshall et al. | |
| 5,779,677 | A | 7/1998 | Frezza | |
| 5,957,896 | A * | 9/1999 | Bendek et al. | 604/207 |
| 7,976,499 | B2 * | 7/2011 | Grunhut et al. | 604/110 |
| 2004/0054326 | A1 | 3/2004 | Hommann et al. | |
| 2006/0264830 | A1 * | 11/2006 | Hommann | 604/136 |
| 2008/0228143 | A1 * | 9/2008 | Stamp | 604/157 |
| 2009/0312705 | A1 * | 12/2009 | Grunhut et al. | 604/110 |

FOREIGN PATENT DOCUMENTS

| DE | 198 19 409 A1 | 11/1999 |
| DE | 100 15 616 A1 | 10/2001 |
| EP | 0 897 728 A1 | 2/1999 |
| WO | 2005/070481 A1 | 8/2005 |
| WO | 2007/132353 A2 | 11/2007 |

* cited by examiner

*Primary Examiner* — Nicholas Lucchesi
*Assistant Examiner* — Aarti B Berdichevsky
(74) *Attorney, Agent, or Firm* — Hoffmann & Baron, LLP

(57) ABSTRACT

The present invention relates to a device for automatic injection of a product into an injection site. The product is being carried by a container having a proximal open-end, a substantially closed distal end, carrying a needle to provide an outlet port for the product from the container and a piston provided in the container and distally movable with respect to the container. The movement of the piston causes the product to be expelled from the container. The device further comprises:
  automatic injection means for causing the piston to move with respect to the container;
  a housing receiving the automatic injection means;
  controlling means cooperating with the automatic injection means to produce an audible indicator when the piston is near the distal end of the container and the product is substantially completely expelled from the container thereby informing a user that injection of the product is completed;
The present invention is characterized in that the controlling means comprise at least an intermediate part coupled to the automatic injection means and at least a flexible part coupled to the housing, the intermediate part cooperating with the flexible part to produce the audible indicator.

11 Claims, 1 Drawing Sheet

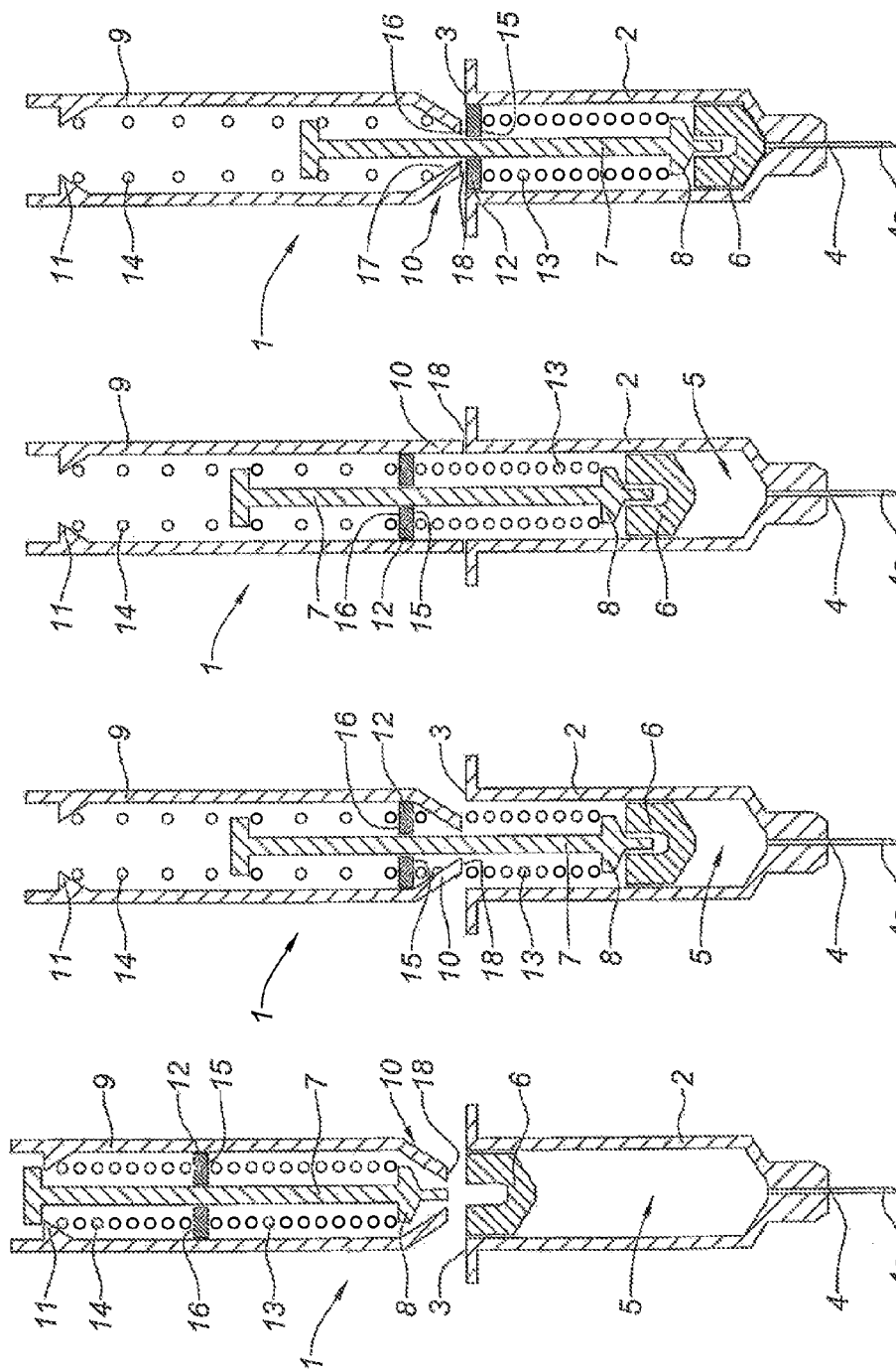

AUTOINJECTOR WITH AUDIBLE INDICATION OF COMPLETED DELIVERY

The present invention relates to a device for automatic injection of a product ensuring the user that the product has been substantially completely injected.

In the present application, the distal end of a component or of a device is to be understood as meaning the end furthest from the user's hand during proper use and the proximal end is to be understood as meaning the end closest to the user's hand during proper use. Likewise, in the present application, "the distal direction" is intended for defining the direction of the injection, and the "proximal direction" for defining the opposite direction to the direction of injection.

Some illnesses necessitate regular injections for drugs or products, for instance on a daily basis. In order to simplify the treatment of such illnesses, some devices for automatic injection have been developed to allow the patient to perform the injection on its own.

Of course, since the patient is usually neither a nurse nor an educated person in medical devices, such devices for automatic injection must prove to be very simple to use and very safe. In particular, it is important to ensure that a controlled dose of a product is injected with such a device, that is to say a complete injection must be performed. Moreover, in some cases, the user may withdraw the device for automatic injection before the injection is completed. It is therefore important for the user to be informed that the product has been substantially completely injected and that he may withdraw the device from the injection site.

It is known from the patent application WO 2007/132353 an automatic injection device wherein a sound is emitted during or at the end of the injection, thereby indicating the patient that the injection is completed when the sound ceases or when the sound is made, respectively.

The present invention proposes a device for automatic injection of a product into an injection site, said device producing an audible indicator when the injection is completed.

The present invention relates to a device for automatic injection of a product into an injection site. The product is being carried by a container having a proximal open-end, a substantially closed distal end, carrying a needle to provide an outlet port for the product from the container and a piston provided in the container and distally movable with respect to the container. The movement of the piston causes the product to be expelled from the container. The device further comprises:

automatic injection means for causing the piston to move with respect to the container;

a housing receiving the automatic injection means;

controlling means cooperating with the automatic injection means to produce an audible indicator when the piston is near the distal end of the container and the product is substantially completely expelled from the container thereby informing a user that injection of the product is completed.

The present invention is characterized in that the controlling means comprise at least an intermediate part coupled to the automatic injection means and at least a flexible part coupled to the housing, the intermediate part cooperating with the flexible part to produce the audible indicator.

The device of the invention allows the user to be clearly informed of the end of injection.

In an embodiment of the present invention, said intermediate part is adapted to deflect said flexible part substantially at the end of the injection, said automatic injection means cooperating with said intermediate part to release said flexible part allowing said at least a flexible part to return to a non-deflected position thereby generating a sound.

The device of the present invention may further comprise a clapping part, said at least a flexible part bumping onto the clapping part when said at least a flexible part comes back to said non-deflected position.

In another embodiment, said automatic injection means comprise at least two elastic means and the intermediate part is located between said at least two elastic means.

In a further embodiment, said housing comprises an inner rim located on its inner wall near its proximal end, and said elastic means comprise a distal coil spring and a proximal coil spring serially mounted, wherein a distal end of said distal coil spring is intended to lean directly or indirectly against the piston and a proximal end of said distal coil spring leans against a distal side of the intermediate part, and wherein a distal end of said proximal spring coil leans against a proximal side of the intermediate part and a proximal end of said proximal coil spring leans against said inner rim.

In a still further embodiment, after said flexible part has returned to its non-deflected position, said intermediate part is prevented to move in the proximal direction by an abutment surface located on said housing. Thus said distal coil spring may remain partly loaded at the end of the injection, thereby causing said piston to be maintained in contact with said distal end of the container.

The device may further comprise a piston rod for pushing the piston distally, said piston rod being provided with a flange at its distal end, the distal end of said distal coil spring leaning against said flange of the piston rod.

In another embodiment of the present invention, said piston rod is received within said distal and proximal coil springs, and said intermediate part comprises a ring mounted sliding around said piston rod.

In another embodiment of the present invention, said distal and proximal coil springs are similar. In another embodiment of the invention, said distal and proximal coil springs are different. In particular, said distal and proximal coil springs can have same or different spring rate.

In another embodiment of the present invention, the clapping part is part of said proximal coil spring.

In another embodiment of the present invention, the intermediate part is made of metal or plastic.

The device of the present invention will now be further described in reference to the following description and attached drawings in which:

FIG. 1 is schematic longitudinal cross section view of a device of the invention, before use;

FIG. 2 is a schematic longitudinal cross section view of the device of FIG. 1 during the injection but before the end of the injection;

FIG. 3 is a schematic longitudinal cross section view of the device of FIG. 1 in a position where the intermediate part cooperate with the at least a flexible part;

FIG. 4 is a schematic longitudinal cross section of the device of FIG. 1 after the end of the injection.

Referring now to the drawings, the present invention will now be described in detail. FIG. 1 shows a schematic longitudinal cross section of a device for automatic injection according to the present invention, as provided to the user before use, and which is referred to as device 1 in the following description. The device 1 comprises a container 2 having a proximal open-end 3, a substantially closed distal end 4 and carries a product 5. A piston 6 is provided in the container 2 and is distally movable with respect to said container 2. As it will appear in the description below, the movement of the piston 6 in the distal direction is intended to cause the product 5 to be expelled from the container 2 through a needle 4a provided at the distal end 4 of the container 2. The device 1 comprises also a piston rod 7 provided with a flange 8 at its distal end to push distally said piston 6. The device further comprises a housing 9 provided at its distal end with a flexible part, a flexible leg 10 on the example shown, and at its proximal end with an inner rim 11 located on the inner wall.

The device 1 further comprises an intermediate part under the form of a ring 12 mounted sliding around said piston rod 7, in the example represented on Figures.

The device 1 further comprises elastic means, which, on the device represented in FIG. 1, are two coil springs serially mounted, a distal coil spring 13 and a proximal coil spring 14. In an embodiment not shown, the elastic means may comprise one or more additional coil springs. In the represented device 1 of the FIG. 1, said piston rod 7 is received within said distal and proximal coil spring 13, 14, wherein said distal coil spring 13 has its proximal end leaning against the distal side 15 of the ring 12 and its distal end leaning against the flange 8. Said proximal coil spring 14 has its proximal end leaning on said inner rim 11, and has its distal end leaning on a proximal side 16 of the ring 12. Before use, the distal and proximal coil springs 13, 14 are loaded. As it will appear later in the description, the proximal and distal coil springs 13, 14 act as automatic injection means and the user initiate the injection by freeing said proximal and distal coil springs 13, 14 with the help of triggering means not shown on figures. The distal and proximal coil spring 13, 14 can be the same or different, in particular, they can have the same or different spring rates.

The device may further comprise an outer sleeve, not shown on figures, receiving the container 2 and the housing 9, and coupling said container 2 and said housing 9.

The FIG. 2 shows a schematic longitudinal cross section view of device 1 in use, after said proximal and distal coil springs 13, 14 have been freed but before the substantial end of the injection. The distal and proximal coil springs 13, 14 have started to expand, thereby pushing on the piston rod 7 in the distal direction. Thus said piston rod 7 have come into contact with the piston 6 and, subsequently causes the piston 6 to move with respect to the container 2, expelling the product 5 from the container 2 and realizing the injection. The ring 12, coupled with the distal and proximal coil springs 13, 14, moves in the distal direction while said distal and proximal coil springs 13, 14 are expanding.

The FIG. 3 shows a schematic longitudinal cross section view of the device 1 in use, close to the end of the injection wherein the ring 12 cooperates with said flexible leg 10. Said flexible leg 10 is deflected outwards by the ring 12 moving in the distal direction, pushed by the proximal coil spring 14. The flexible leg 10 is maintained in its deflected position as long as the ring 12 puts a strain on said flexible leg 10.

On FIG. 4 is shown the device 1 at the end of the injection. The piston 6 is into contact with the distal end 4 of the container 2 and the product 5 has been substantially completely expelled. The ring 12 is located outside the housing 9 and said flexible leg 10 is in the non-deflected position. Substantially at the end of the injection, while the ring 12 is still moving in the distal direction, the proximal side 16 of said ring 12 comes at the level of the distal end of said flexible leg 10 and, once the ring 12 moves forward said strain is released, causing said flexible leg 10 to come back in its non-deflected position. While returning to said non-deflected position, said flexible leg 10 bumps onto a clapping part 17 thereby producing a sound. On the example shown, the clapping part 17 is a part of said distal coil spring 13. The audible indicator or sound thus produced informs the user the injection is completed and that the product 5 has been substantially completely expelled from the container 2. In another embodiment not represented, the clapping part is an additional piece, separated or not from said distal coil spring; this additional piece may be made of plastic. As it appears from the figures, the ring 12 and the flexible leg 10 act as controlling means cooperating with the automatic injection means, ie the coil springs (13, 14) to produce an audible indicator when said piston (6) is near said distal end (4) of the container (2) and the product (5) is substantially completely expelled from the container (2) thereby informing a user that injection of the product (5) is completed.

In the position shown on FIG. 4, the ring 12 is prevented to move back in the proximal direction by an abutment surface 18 located on the housing 9 and corresponding, on the example shown, to the distal end of the flexible leg 10. This abutment surface 18 maintains the ring 12 outside the housing 9 and said distal coil spring 13 partly loaded, ensuring that the piston 6 remains in its final position against the distal end 4 of said container 2. Once the injection is completed, the user removes the device 1 from the injection site.

The ring 12 can be made of different thickness, as long as it is adapted to come in contact with said abutment surface 18, substantially at the end of the injection but not before. In particular, in a embodiment not shown of the present invention, the ring can have a thickness so that it deflects said at least a flexible leg 10 all along the injection, or most of the time of the injection, and releases said strain on said at least a flexible leg 10 substantially and only substantially at the end of the injection.

The invention claimed is:

1. Device for automatic injection of a product into an injection site, the product being carried by a container having a proximal open-end, a substantially closed distal end, carrying a needle to provide an outlet port for the product from the container and a piston provided in the container and distally movable with respect to the container, the movement of the piston causing the product to be expelled from the container, said device further comprising:
   automatic injection means for causing the piston to move with respect to the container;
   a housing receiving the automatic injection means;
   controlling means cooperating with the automatic injection means to produce an audible indicator when said piston is near said distal end of the container and the product is substantially completely expelled from the container thereby informing a user that injection of the product is completed;
   characterized in that said controlling means comprise at least an intermediate part coupled to the automatic injection means and at least a flexible part coupled to the housing, said intermediate part is adapted to deflect said flexible part substantially at the end of the injection, said automatic injection means cooperating with said intermediate part to release said flexible part allowing said flexible part to return to a non-deflected position thereby generating a sound.

2. Device for automatic injection according to claim 1, further comprising a clapping part, said at least a flexible part bumping onto the clapping part when said at least a flexible part comes back to said non-deflected position.

3. Device for automatic injection according to claim 1, characterized in that said automatic injection means comprise at least two elastic means and in that the intermediate part is located between said at least two elastic means.

4. Device for automatic injection of a product into an injection site, the product being carried by a container having a proximal open-end, a substantially closed distal end, carrying a needle to provide an outlet port for the product from the container and a piston provided in the container and distally movable with respect to the container, the movement of the piston causing the product to be expelled from the container, said device further comprising:

automatic injection means for causing the piston to move with respect to the container, said automatic injection means comprise at least two elastic means;

a housing receiving the automatic injection means, said housing comprises an inner rim located on its inner wall near its proximal end;

controlling means cooperating with the automatic injection means to produce an audible indicator when said piston is near said distal end of the container and the product is substantially completely expelled from the container thereby informing a user that injection of the product is completed;

characterized in that said controlling means comprise at least an intermediate part coupled to the automatic injection means, and located between said at least two elastic means, and at least a flexible part coupled to the housing said intermediate part cooperating with the flexible part to produce said audible indicator, and characterized in that said elastic means comprise a distal coil spring and a proximal coil spring serially mounted, wherein a distal end of said distal coil spring is intended to lean directly or indirectly against the piston and a proximal end of said distal coil spring leans against a distal side of the intermediate part, and wherein a distal end of said proximal spring coil leans against a proximal side of the intermediate part and a proximal end of said proximal coil spring leans against said inner rim.

5. Device for automatic injection according to claim 4, characterized in that after said flexible part has returned to its non-deflected position, said intermediate part is prevented to move in the proximal direction by an abutment surface located on said housing.

6. Device for automatic injection according to claim 4, characterized in that said distal and proximal coil springs are similar.

7. Device for automatic injection according to claim 4, characterized in that said distal and proximal coil springs are different.

8. Device for automatic injection according to claim 4, further comprising a clapping part, said at least a flexible part bumping onto the clapping part when said at least a flexible part comes back to said non-deflected position, and characterized in that the clapping part is part of said distal coil spring.

9. Device for automatic injection according to claim 1, characterized in that intermediate part is made of metal or plastic.

10. Device for automatic injection according to claim 4, characterized in that the device further comprises a piston rod for pushing the piston distally, said piston rod being provided with a flange at its distal end, and in that the distal end of said distal coil spring leans against said flange of the piston rod.

11. Device for automatic injection according to claim 10, characterized in that said piston rod is received within said distal and proximal coil spring, and in that said intermediate part comprises a ring mounted sliding around said piston rod.

\* \* \* \* \*

UNITED STATES PATENT AND TRADEMARK OFFICE
CERTIFICATE OF CORRECTION

PATENT NO. : 8,366,668 B2  Page 1 of 1
APPLICATION NO. : 13/120769
DATED : February 5, 2013
INVENTOR(S) : Lionel Maritan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3 days.

Signed and Sealed this
First Day of September, 2015

Michelle K. Lee
*Director of the United States Patent and Trademark Office*